(12) United States Patent
Choi et al.

(10) Patent No.: US 8,729,052 B2
(45) Date of Patent: May 20, 2014

(54) COMPOSITION FOR THE PREVENTION AND TREATMENT OF ALOPECIA, OR FOR HAIR GROWTH

(75) Inventors: Myeong Jun Choi, Gyunggido (KR); Joo Hyun Cho, Kangwondo (KR)

(73) Assignee: Phytos Co., Ltd., Gyeonggi-do (KR)

( * ) Notice: Subject to any disclaimer, the term of this patent is extended or adjusted under 35 U.S.C. 154(b) by 272 days.

(21) Appl. No.: 13/057,646

(22) PCT Filed: Jul. 30, 2009

(86) PCT No.: PCT/KR2009/004254
§ 371 (c)(1),
(2), (4) Date: Mar. 30, 2011

(87) PCT Pub. No.: WO2010/016683
PCT Pub. Date: Feb. 11, 2010

(65) Prior Publication Data
US 2012/0004439 A1    Jan. 5, 2012

(30) Foreign Application Priority Data
Aug. 6, 2008 (KR) .......................... 10-2008-0076739

(51) Int. Cl.
*A01N 65/00* (2009.01)
(52) U.S. Cl.
USPC .................... 514/70; 514/72; 514/73; 514/74

(58) Field of Classification Search
CPC ....................................................... A61K 8/553
USPC .......................................... 514/70, 72, 73, 74
See application file for complete search history.

(56) References Cited

U.S. PATENT DOCUMENTS 6,184,252 B1    2/2001  Fagot et al.
6,964,952 B2 *  11/2005 Park et al. ..................... 514/110

FOREIGN PATENT DOCUMENTS

| JP | H05-25023 A | 2/1993 |
| JP | H09-227343 A | 9/1997 |
| JP | 2000-109409 A | 4/2000 |
| JP | 2001-278750 A | 10/2001 |
| KR | 1998-0071959 | 10/1998 |
| KR | 2007-0026580 A | 3/2007 |
| KR | 10-1003532 A | 12/2010 |

OTHER PUBLICATIONS

Won-Soo Lee et al., "Integral lipid in human hair follicle", J Investig Dermatol Symp Proc. Dec. 2005; 10(3):234-7.
K. Yano et al. "Control of hair growth and follicle size by VEGF-mediated angiogenesis.", Journal of Clinical Investigation, vol. 107, No. 4, 409-417, Feb. 2001.

* cited by examiner

*Primary Examiner* — Yong Chong
(74) *Attorney, Agent, or Firm* — Rabin & Berdo, P.C.

(57) ABSTRACT

Disclosed is a composition for prevention and treatment of alopecia or for hair growth, comprising a phytosphingosine-1-phosphate derivative or a pharmaceutically acceptable salt thereof as an active ingredient. Also, a medicine comprising the composition and a quasi-drug comprising the composition are provided.

1 Claim, 3 Drawing Sheets

COMPOSITION FOR THE PREVENTION AND TREATMENT OF ALOPECIA, OR FOR HAIR GROWTH

FIELD OF THE INVENTION

The present invention relates to a composition for the prevention and treatment of alopecia, or for hair regrowth. More particularly, the present invention relates to a composition for hair regrowth, or for the treatment of hair loss, comprising phytosphingosine as an active ingredient.

BACKGROUND OF THE INVENTION

As males become physically masculinized, the male body is characterized by the buildup of skeletal muscle, the maturation of the genital organ, the growth of spermatogenic tissue in the testicles, and sexual inclination; all of which are backed by testosterone, with the concomitant occurrence of dihydrotestosterone-mediated negative conditions including the generation of acne, enlargement of sebaceous glands, alopecia, and benign prostatic hyperplasia. Hair loss, mostly found in men, has long been studied, but the causes of hair loss and growth have yet to be proven. There is increasingly an imperative need for the prevention and treatment of hair loss because hair has greater social significance for people in many aspects, including aesthetics in modern society.

Hair is an organism that follows a specific growth cycle with three phases of anagen, catagen and telogen. Strands of hair independently experience growth cycle phases, so that the number of hair is kept nearly constant. The number of hairs on any individual is actually determined at birth. In many cases, the maturation of hairs by sex hormones is mistaken for an increase in the number of hairs.

The anagen phase is known as the growth phase, during which the cells in the papilla actively divide to produce new hair fibers, and the follicle buries itself into the dermal layer of the skin to nourish the strand. The anagen phase lasts about 2~6 years. About 85% of the hairs on one's head are in the anagen phase at any given time. Around the papilla is the hair matrix, a collection of epithelial cells in the form of a bulb. In the anagen phase, these cells are constantly dividing, adding to the hair shaft. The catagen phase is a short transition phase in which the follicle rapidly shrinks, with its growth activity stopped. This phase lasts for about 2~3 weeks while club hair is formed. The catagen phase accounts for about 5% of the hairs on one's head in a given time. The telogen phase is the resting phase in which the cellular activity of the hair follicle remain dormant. It lasts about 2~3 months, during which the preceding club hair is pushed up and out by the new, growing strand or normally lost by mechanical actions, for example, by combing or washing one's head. Generally, alopecia is the term for the abnormal loss of hair which results from a reduction in the proportion of the hair in the anagen phase to that in the catagen or telogen phase.

Alopecia is caused by various factors including the action of male sex hormones, mental stress, the accumulation of lipid peroxide, side-effects from drugs or radiotherapy, chronic diseases such as leukemia and tuberculosis, malnutrition, etc. Recently, hair loss, which has been regarded as a male ailment, is now frequently found in women and the youth, with increasing demand for the prevention and treatment of hair loss.

Among medications for use in promoting hair growth, or as hair tonics, there are now vasodilators for promoting the circulation of sufficient blood to the scalp, female hormones for suppressing the action of male hormones, and male hormone inhibitors for suppressing the activity of 5α-reductase which converts testosterone into 5-DHT (5-dihydrotesteone). Examples of the vasodilators include carpronium chloride, minoxidil and various plant extracts. Within the range of the useful female hormones are estrogen, estradiol and progesterone. The male hormone inhibitors are exemplified by finateride and pentadecanoic acid.

SUMMARY OF THE INVENTION

Technical Problem

Leading to the present invention, intensive and thorough research into the treatment and prevention of alopecia and the promotion of hair growth, conducted by the present inventors, aiming to overcoming the problems encountered in the prior art, resulted in the finding that phytosphingosine-1-phosphate derivatives are effective for treating and preventing alopecia and for promoting hair growth.

It is therefore an object of the present invention to provide a composition for the prevention and treatment of alopecia and for hair growth, comprising a phytosphingosine-1-phosphate derivative as an active ingredient.

It is another object of the present invention to provide medication for use in the prevention and treatment of alopecia and in the promotion of hair growth.

It is a further object of the present invention to provide a quasi-drug comprising the composition for the prevention and treatment of alopecia and for hair growth.

Technical Solution

As a result of intensive and thorough studies, the present inventors succeeded in developing agents effective for the prophylaxis and treatment of alopecia and for hair growth, which is based on phytosphingosine-1-phosphate derivatives.

Therefore, an object of the present invention is to provide a composition for the prevention and treatment of alopecia and for hair growth, comprising a phytosphingosine-1-phosphate derivative as an active ingredient.

Another object of the present invention is to provide a medicine for use in the prevention and treatment of alopecia and in the promotion of hair growth.

A further object of the present invention is to provide a quasi-drug comprising the composition for the prevention and treatment of alopecia and for hair growth.

In order to accomplish the above objects, the present invention provides a composition for the prevention and treatment of alopecia and for hair growth, comprising a compound represented by the following chemical formula 1 or a pharmaceutically acceptable salt thereof:

[Chemical Formula 1]

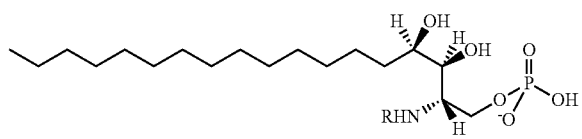

wherein R is hydrogen or —COR$^1$ wherein R1 is $C_1$-$C_6$ alkyl.

Also, the present invention provides a medicine comprising the composition for the composition for the prevention and treatment of alopecia and for hair growth.

Further, the present invention provides a quasi-drug comprising the composition for the prevention and treatment of alopecia and for hair growth.

Hereinafter, embodiments of the present invention will be described in detail while referring to the accompanying drawings.

Unless defined otherwise, the terms and words used in the present specification and claims should be interpreted as having meanings and concepts relevant to the technical scope of the present invention. Furthermore, although the invention has been described in conjunction with specific methods and samples, their analogs or equivalents should be within the scope of the present invention. All the publications mentioned are incorporated by reference in their entirety.

At the end of the study on the development of an agent useful for preventing and treating alopecia and for promoting hair growth, the present inventor found derivatives of phytosphingosine, a natural chemical currently used as an ingredient of a moisturizing agent or an acne therapeutic, and showed the activity of preventing and treating alopecia and promoting hair growth to the extent as great as or greater than that of minoxidil, without incurring the side-effects of minoxidil, including dermal irritation, and cautious administration to hypertensive patients. Based on the finding, the present inventors developed a pharmaceutical composition for the prophylaxis and treatment of alopecia and for hair regrowth.

In accordance with an aspect thereof, the present invention provides a composition for the prevention and treatment of alopecia or for promoting hair regrowth, comprising a compound represented by the following Chemical Formula 1, or a pharmaceutically acceptable salt thereof as an active ingredient:

[Chemical Formula 1]

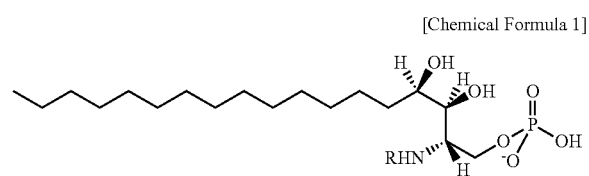

wherein, R is hydrogen or —COR$^1$ wherein R$^1$ is C$_1$-C$_6$ alkyl. Preferably, R is hydrogen or C$_1$-C$_3$ alkyl.

The compound of Chemical Formula 1 can be synthesized using the ordinary knowledge well known in the organic chemistry, for example, using a method disclosed in S. Li, W. K. Wilson, G. J. Schroepfer, Chemical synthesis of D-ribo-phytosphingosine-1-phosphate, a potential modulator of cellular processes. J. Lipid Res. 40: 117-125, 1999.

As will be proven in the following Example section, the compound of Chemical Formula 1 is very effective for the prevention and treatment of alopecia and for hair growth. In greater detail, the compound of the present invention was found to show as useful a hair growth effect as that of Rogaine (Minoxidil 5% solution, Johnson and Johnson), a commercially available drug approved by the FDA for treating hair loss. In addition, the compound of the present invention was analyzed for angiogenic activity by CAM (chorioallantoic membrane) assay, with the use of phosphate buffered saline as a negative control, sphingosine-1-phosphate as a positive control, and the angiogenesis inhibitor TMP (trimethylhytosphingosine) as a suppressive control. In comparison to the controls, the compound of the present invention showed a remarkably excellent effect on angiogenesis. Therefore, the compound of Chemical Formula 1 in accordance with the present invention is anticipated to exert a prophylactic and therapeutic effect on alopecia and a promotive effect on hair growth on the basis of its excellent angiogenic activity.

The composition according to the present invention may be used as a complex agent further comprising another drug or supplementary which is preventive and therapeutic of alopecia or promotive of hair growth. Examples of the drug or supplementary useful in the present invention include retinoic acid, minoxidil, finasteride, zinc peptide, zinc oxide, biotin, genistein, an onion extract, pumpkin seed oil, Emu oil, a green tea extract, and a willow bark extract, but are not limited thereto.

The composition of the present invention may be formulated into oral forms, injections, suppositories, transdermal agents and intranasal agents, and any other dosage form. Preferable is a topical formulation which can be applied to the scalp or hairy head. Examples of the topical formulation include liposomes, nano-emulsions, shampoos, hair conditioners, and hair lotions, but are not limited thereto. Preferably, the composition may be formulated into liposomes or nano-emulsions because their transdermal absorption into the body promotes the desired effect. Upon the preparation of the composition into formulations, pharmaceutically acceptable additives known to be suitable for formulations, such as carries, diluents, excipients, etc., may be used.

Based on the total weight of the composition of the present invention, the compound of Chemical Formula 1 may be contained in an amount of from about 0.1% to 10% by weight and preferably in an amount of from about 0.5% to 5% by weight. Its amount may be increased or decreased depending on the kinds of the compound of Chemical Formula 1.

For topical use, the composition according to the present invention may be applied to a region in need of the prevention and treatment of alopecia or in need of hair growth once or twice a day. A composition comprising the active ingredient in an amount of 1% by weight is applied at a daily dose of 0.5~3 mg. The dose may be dependent on the application area. Also, the administration of the composition may vary in dose and frequency depending on various factors including patient's age and gender and the progression of alopecia.

Not only does the compound of Chemical Formula 1 or a pharmaceutically acceptable salt thereof show excellent therapeutic and preventive effects on alopecia and promotive effects on hair growth, but also it can be easily synthesized thanks to the simple chemical structure thereof. When formulated into lipid particles such as liposomes and nano-emulsion, the compound of the present invention can be easily transferred to the follicle. Further, the compound of the present invention neither irritates the skin nor causes side-effects, unlike the conventional drugs minoxidil and finasteride.

The composition comprising the compound of Chemical Formula 1 as an active ingredient for the prevention and treatment of alopecia and for hair growth may be formulated into a medicine product or a quasi-drug product for the same purpose.

Therefore, in accordance with another aspect thereof, the present invention provides a medicine or quasi-drug comprising the composition of the present invention and a pharmaceutically acceptable carrier or additive.

Advantageous Effect

As described hitherto, the composition in accordance with the present invention is highly effective for the prevention and treatment of alopecia and for hair growth, without causing dermal irritation or side-effects in contrast to the conventional hair loss drugs such as minoxidil and finasteride, and can be easily transferred to the hair follicle when it is formulated into lipid microparticles such as liposomes or nano-emulsions. In addition, the compound of Chemical Formula 1 is so simple in chemical structure that it can be easily synthesized, with an economical benefit.

DESCRIPTION OF THE PREFERRED EMBODIMENTS

Modes for Invention

Figure 1:
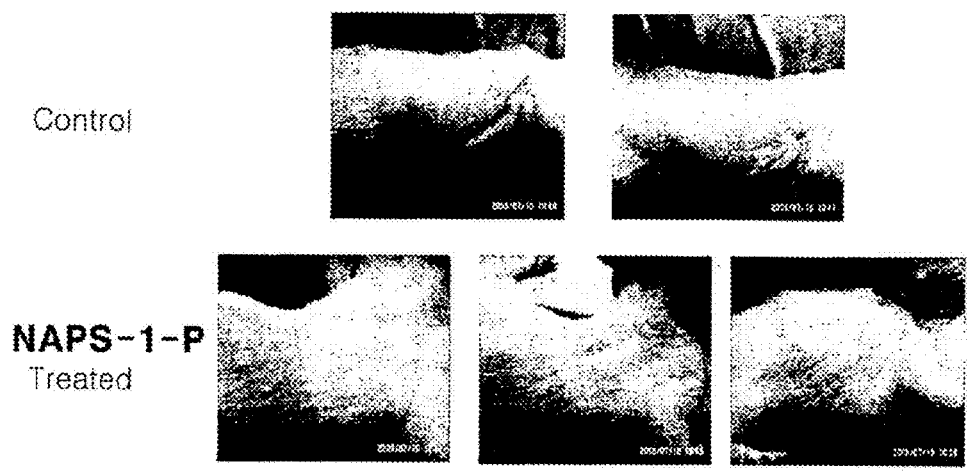
FIG. 1 shows photographs of balb/c mice which were depilated on their sides and then coated with N-acetylphytosphingosine-1-phosphate (NAPS-1-P)-containing liposomes for the depilated areas once a day to a total of coating rounds, in comparison with non-treated mice.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples:

EXAMPLE 1

Preparation of Liposome Containing N-Acetylphytosphingosine-1-phosphate (NAPS-1-P) (1)

Liposomes containing N-acetylphytosphingosine-1-phosphate (NAPS-1-P) therein were prepared. NAPS-1-P was synthesized according to the method disclosed in S. Li, W. K. Wilson, G. J. Schroepfer, Chemical synthesis of D-ribo-phytosphingosine-1-phosphate, a potential modulator of cellular processes. J. Lipid Res. 40: 117-125, 1999. For this, first, 3 g of 75% soybean phosphatidyl choline (Lipoid) and 0.5 g of NAPS-1-P were dissolved in 20 g of ethanol. To the solution of phosphatidyl choline and NAPS-1-P in ethanol was slowly added a solution of 0.1 g of menthol in 76.4 g of distilled water, with vigorous stirring. After completion of the addition, the resulting solution was continuously stirred for one hour. It was ultrasonicated using a Tip-type sonicator, followed by filtration through a 0.22 μm membrane filter to produce liposomes containing NAPS-1-P 0.5%. To them, a mixture of poloxamer+polysorbate 20 (Tween 20) was added as a skin penetration enhancer to give a nano-emulsion according to the present invention.

EXAMPLE 2

Preparation of Liposomes Containing NAPS-1-P Therein (2)

NAPS-1-P 1.0%-containing liposomes were prepared in the same manner as in Example 1, with the exception that NAPS-1-P was used in an amount of 1 g, instead of 0.5 g. In this context, a peony bark extract and a willow bark extract were used in a predetermined amount while the amount of distilled water was reduced as much.

EXAMPLE 3

Preparation of Liposomes Containing NAPS-1-P Therein (3)

The same procedure as in Example 1 was repeated, with the exception that 3 g of a peony bark extract and 5 g of a willow bark extract were added together with the distilled water, and NAPS-1-P was used in an amount of 1.0 g instead of 0.5 g. In this context, the peony bark and the willow bark extract were used in a predetermined amount while the amount of distilled water was reduced as much.

EXAMPLE 4

Preparation of Liposomes Containing Phytosphingosine-1-phosphate (PhS-1-P) Therein (3)

PhS-1-P 0.5%-containing liposomes were prepared in the same manner as in Example 1, with the exception that phytosphingosine-1-phosphate (PhS-1-P) was used instead of NAPS-1-P.

The compositions of the liposomes prepared in Examples 1 to 4 are summarized in Table 1, below.

TABLE 1

Composition of Liposomes Containing NAPS-1-P and PhS-1-P

| Composition | Ex. 1 | Ex. 2 | Ex. 3 | Ex. 4 |
|---|---|---|---|---|
| NSPS-1-P | 0.5 | 1.0 | 1.0 | 0 |
| PhS-1-P | 0 | 0 | 0 | 0.5 |
| Lecithin | 3 | 3 | 3 | 3 |
| Ethanol | 20 | 20 | 20 | 20 |
| Menthol | 0.1 | 0.1 | 0.1 | 0.1 |
| Poloxamer | 0.5 | 0.5 | 0.5 | 0.5 |
| Tween 20 | 0.5 | 0.5 | 0.5 | 0.5 |
| Peony bark extract | 0 | 0 | 3 | 0 |
| Willow bark extract | 0 | 0 | 5 | 0 |
| Distilled water | 75.4 | 74.9 | 66.9 | 75.4 |
| Total | 100.0 | 100.0 | 100.0 | 100.0 |

EXAMPLE 5

Preparation of Nano-Emulsion Containing NAPS-1-P Therein (1)

An N-acetylphytosphingosine-containing nano-emulsion was prepared. For this, first, 2 g of 75% soybean phosphatidyl choline (Lipoid) and 0.5 g of NAPS-1-P were dissolved in 15 g of ethanol. To this ethanol solution were added 15 g of PEG-8 caprylic/capric glyceride (LAS) and 3.0 g of isopropylmyristate. Then, after addition of a solution of 0.1 g of menthol in 57.4 g of distilled water to the ethanol solution, gently stirring for 30 min to one hr produced a nano-emulsion. To this, a mixture of poloxamer+polysorbate 20 (Tween 20) was added as a skin penetration enhance to afford a nano-emulsion according to the present invention.

EXAMPLE 6

Preparation of Nano-Emulsion Containing NAPS-1-P Therein (2)

An NAPS-1-P 1.0%-containing nano-emulsion was prepared in the same manner as in Example 5, with the exception that NAPS-1-P was used in an amount of 1.0 g instead of 0.5 g. In this context, the amount of distilled water was reduced as much as the increased amount of NAPS-1-P.

EXAMPLE 7

Preparation of Nano-Emulsion Containing NAPS-1-P Therein (3)

The same procedure as in Example 5 was repeated, with the exception that 3 g of a peony bark extract and 5 g of a willow bark extract were added together with the distilled water, and NAPS-1-P was used in an amount of 1.0 g instead of 0.5 g. In this context, the peony bark extract and the willow bark extract were used in a predetermined amount while the amount of distilled water was reduced as much.

EXAMPLE 8

Preparation of Nano-Emulsion Containing Phytosphingosine-1-phosphate (PhS-1-P) Therein (3)

A PhS-1-P 0.5%-containing nano-emulsion was prepared in the same manner as in Example 5, with the exception that phytosphingosine-1-phosphate (PhS-1-P) was used instead of NAPS-1-P.

The compositions of the nano-emulsions prepared in Examples 5 to 8 are summarized in Table 2, below.

TABLE 2

Composition of Nano-Emulsions Containing NAPS-1-P and PhS-1-P

| Composition | Ex. 5 | Ex. 6 | Ex. 7 | Ex. 8 |
|---|---|---|---|---|
| NAPS-1-P | 0.5 | 1.0 | 1.0 | 0 |
| PhS-1-P | 0 | 0 | 0 | 0.5 |
| lecithin | 2 | 2 | 2 | 2 |
| LAS | 15 | 15 | 15 | 15 |
| IPM | 3 | 3 | 3 | 3 |
| Ethanol | 15 | 15 | 15 | 15 |
| Peony bark extract | 0 | 0 | 3 | 0 |
| Willow bark extract | 0 | 0 | 5 | 0 |
| Menthol | 0.1 | 0.1 | 0.1 | 0.1 |
| Poloxamer | 1 | 2 | 2 | 1 |
| Tween20 | 1 | 2 | 2 | 1 |
| Distilled water | 55.4 | 52.9 | 46.9 | 55.4 |
| Total | 100.0 | 100.0 | 100.0 | 100 |

EXPERIMENTAL EXAMPLE 1

Test for Hair Growth in Balb/c Mice (1)

Balb/c mice, 5-6 weeks old, were purchased and shaved on the side to remove hair partially, followed by applying a depilatory cream to the shaved area to remove hair therefrom completely. The mice which were not completely depilated were excluded from the test. The suitable mice were randomly housed in cages at a population of three per cage. A total of five cages were employed.

The mice were left for one day after hair removal, and then the depilated area was coated once a day with the NAPS-1-P-containing liposomes prepared in Example 1. A total of 14 rounds of application were conducted. Hair growth was compared between treated groups and non-treated groups. After rounds of application, the depilated areas were photographed, as shown in FIG. 1.

As seen in FIG. 1, the non-treated groups had the depilated areas exposed to the outside because hair was not or little grown in the depilated areas whereas hair was grown in the depilated skin areas of the treated groups to the extent that they were difficult to discriminate from non-shaved areas. Therefore, it is apparent from the results that the compound of the present invention can promote hair growth.

EXPERIMENTAL EXAMPLE 2

Test for Hair Growth in Balb/c Mice (2)

The NAPS-1-P 0.5%-containing liposomes (Example 1), the NAPS-1-P 1.0%-containing liposomes (Example 2), and the PhS-1-P 0.5%-containing liposomes (Example 4) were tested for hair growth activity in the same manner as in Experimental Example 1, with the exception that they were applied once a day for four weeks. In this context, Rogaine 5% (minoxidil 5% solution) was used as a positive control. The depilated areas were photographed and the results are shown in FIGS. 2 and 3.

Figure 2:
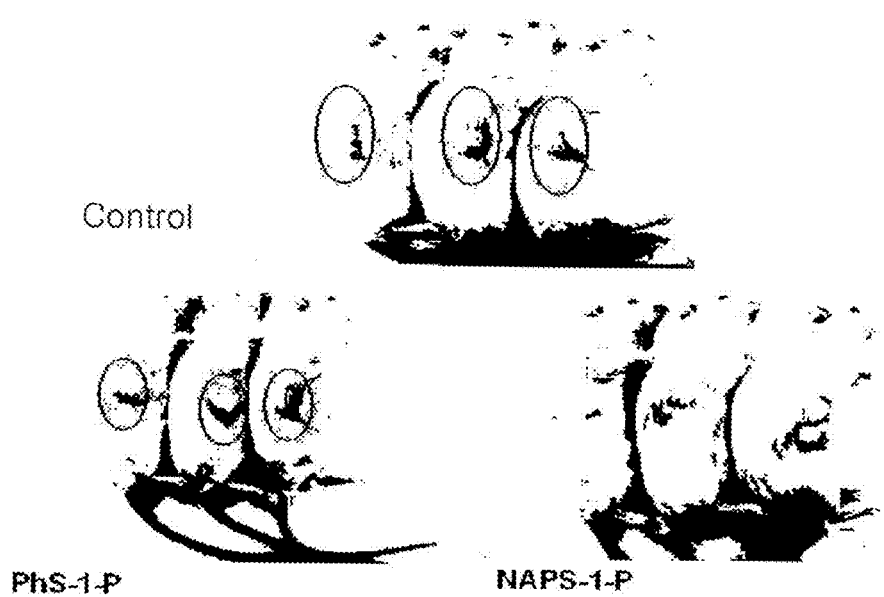
FIG. 2 shows photographs of balb/c mice which were depilated on their sides and then coated with phytosphingosine-1-phosphate (PhS-1-P)-containing liposomes for the depilated areas once a day for four weeks, in comparison with non-treated mice.

FIG. 2 is of photographs of the mice coated with PhS-1-P liposomes and NAPS-1-P liposomes and the control mice. FIG. 3 is of photographs of the mice coated with NAPS-1-P 0.5%-containing liposomes, NAPS-1-P 1.0%-containing liposomes, and a 5% minoxidil solution and the control mice.

Compared to the control, as seen in FIG. 2, both the PhS-1-P liposomes and the NAPS-1-P liposomes were found to have high activity of promoting hair growth, but with superior of NAPS-1-P to PhS-1-P.

Figure 3:
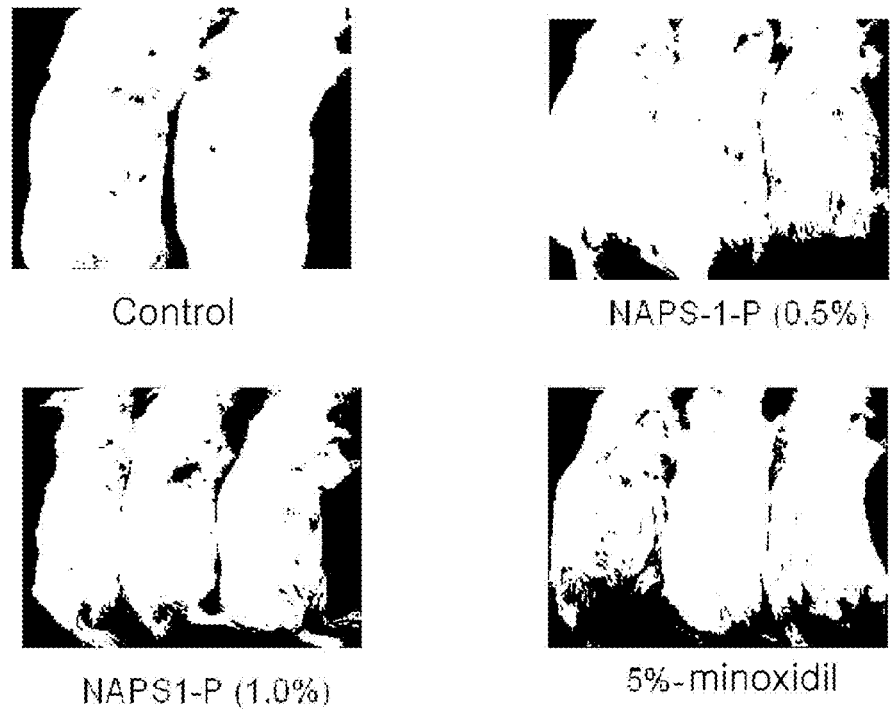
FIG. 3 shows photographs of balb/c mice which were depilated on their sides and then coated with NAPS-1-P 0.5%-containing liposomes, NAPS-1-P 1.0%-containing liposomes and a 5% minoxidil solution once a day for four weeks, in combination with the control.

As is apparent from the photographs of FIG. 3, the NAPS-1-P liposomes were observed to promote hair growth more efficiently at a concentration of 1.0% than 0.5%, so that the hair growth promoting activity was increased in a dose-dependent manner. In addition, the NAPS-1-P 1%-containing liposomal agent was also found to have a therapeutic and preventive effect on hair loss as high as or higher than the minoxidil 5% solution, a currently used hair loss drug.

EXPERIMENTAL EXAMPLE 3

Test for Angiogenic Activity

NAPS-1-P 0.5%-containing liposomes and the PhS-1-P 0.5%-containing liposomes, respectively prepared in Examples 1 and 4, were assayed for angiogenesis, with the use of phosphate buffered saline as a negative control, sphingosine-1-phosphate (PS-1-P) as a positive control, and the angiogenesis inhibitor trimethyl phytosphingosine (TMP) as a suppressive control.

For angiogenesis assay, CAM (chorioallantoic membrane) was used as a model. CAM from developing chicken eggs is routinely used in biological and biomedical research to investigate angiogenesis.

Figure 4:
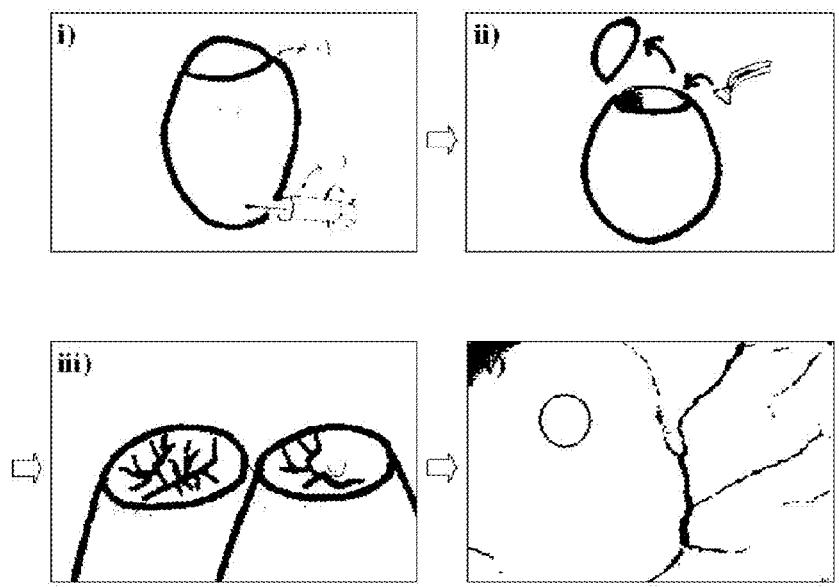
FIG. 4 shows schematic diagrams of a CAM assay process stepwise.

Fertile hen's eggs which were within one day after being laid, were purchased. Three days later, 6 mL of the white was removed from the fertile hen's eggs using a syringe, as illustrated in i of FIG. 4. Afterward, the eggs were opened at the top, as illustrated in ii of FIG. 4. From three days after egg-laying, the embryo started to develop. The membrane surrounding the embryo is CAM. Then, a cover slip on which a test drug was dropwise loaded and dried was placed on CAM, as illustrated in iii of FIG. 4. After the lapse of three days, the eggs were examined for drug-induced angiogenesis under a microscope, as illustrated in iv of FIG. 4.

Figure 5:
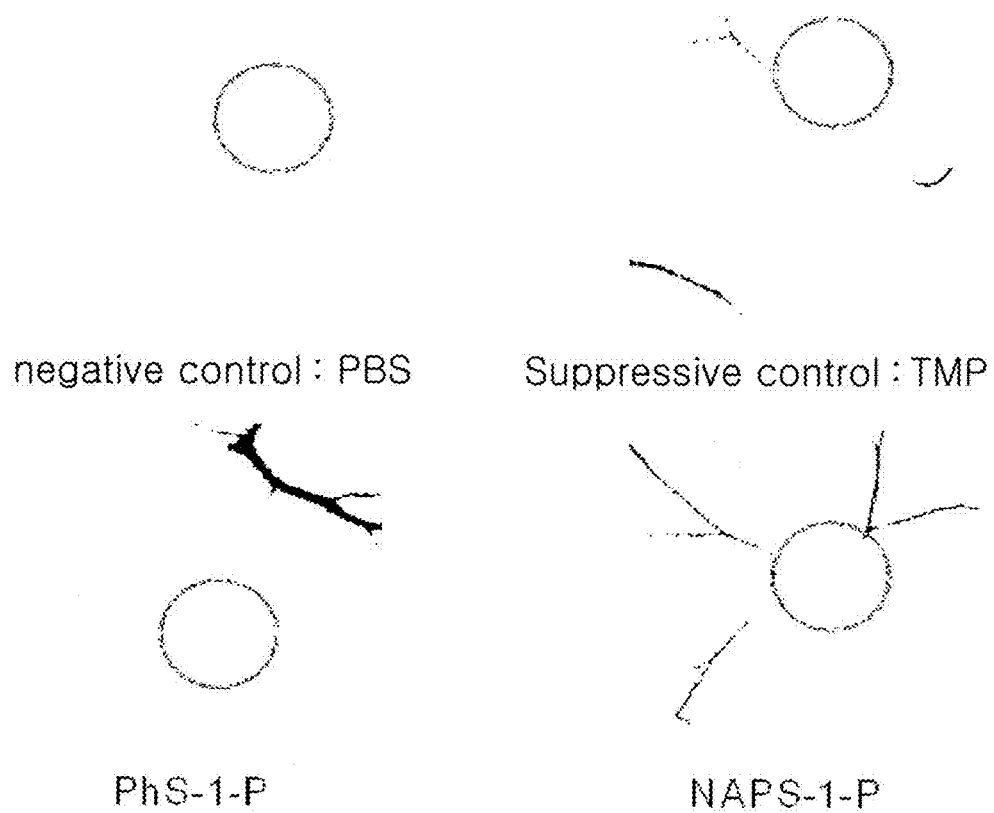
FIG. 5 shows microphotographs of the results of the CAM assay of NAPS-1-P 0.5%-containing liposomes, PhS-1-P 0.5%-containing liposomes, trimethylphytosphingosine (TMP) and phosphate buffered saline for angiogenesis.

With regard to results obtained from the assay of NAPS-1-P 0.5%-containing liposomes, PhS-1-P 0.5%-containing liposomes, TMP, and phosphate buffered saline for angiogenesis, microscopic observation results are summarized in Table 3, and given in FIG. 5.

TABLE 3

| Angiogenesis Results | | | | | | |
|---|---|---|---|---|---|---|
| Group | -- | - | 0 | +/- | + | ++ |
| PBS |  |  | 2 | 8 |  |  |
| TMP | 8 | 2 |  |  |  |  |
| PS-1-P |  |  |  | 1 | 5 | 4 |

TABLE 3-continued

| Angiogenesis Results | | | | | | |
|---|---|---|---|---|---|---|
| Group | -- | - | 0 | +/- | + | ++ |
| PhS-1-P |  |  |  | 1 | 5 | 4 |
| NAPS-1-P |  |  |  |  | 3 | 7 |

--: highly inhibitive of angiogenesis
-: weakly inhibitive of angiogenesis
0: no effects
+/-: insignificantly promotive of angiogenesis
+: weakly promotive of angiogenesis
++: highly promotive of angiogenesis As is apparent from the data of Table 5 and FIG. 5, both PhS-1-P and NAPS-1-P, useful as an active ingredient of the composition of the present invention, showed significant angiogenic activity, compared to the control, with a peak activity found from NAPS-1-P.

What is claimed is:

1. A method for treating alopecia to a patient with alopecia comprising administering a therapeutically effective amount of a compound of Formula I, or a pharmaceutically acceptable salt thereof:

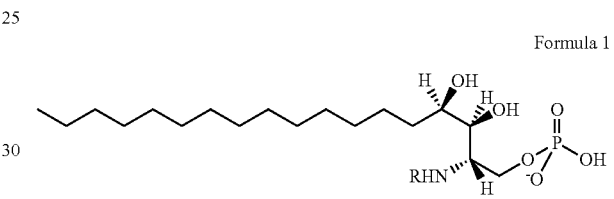

Formula 1 wherein, R is hydrogen or —COR$^1$ wherein R$^1$ is $C_1$-$C_6$ alkyl.

* * * * *